United States Patent
Henderson et al.

(10) Patent No.: US 7,762,940 B2
(45) Date of Patent: *Jul. 27, 2010

(54) DIRECTIONALLY EMITTING RADIOACTIVE SOURCES FOR BRACHYTHERAPY

(75) Inventors: Douglass L. Henderson, Madison, WI (US); Liyong Lin, Madison, WI (US); Bruce R. Thomadsen, Madison, WI (US); Wendy C. Crone, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1114 days.

This patent is subject to a terminal disclaimer.

(21) Appl. No.: 11/130,967

(22) Filed: May 17, 2005

(65) Prior Publication Data

US 2005/0261541 A1 Nov. 24, 2005

Related U.S. Application Data

(60) Provisional application No. 60/572,962, filed on May 20, 2004.

(51) Int. Cl.
*A61M 36/12* (2006.01)
*A61N 5/00* (2006.01)
(52) U.S. Cl. .............................. 600/8; 600/7
(58) Field of Classification Search ............ 600/1–8, 600/37; A61M 36/12
See application file for complete search history.

(56) References Cited

U.S. PATENT DOCUMENTS

| | | | | |
|---|---|---|---|---|
| 5,415,169 A | * | 5/1995 | Siczek et al. | 600/427 |
| 6,080,099 A | * | 6/2000 | Slater et al. | 600/8 |
| 6,264,599 B1 | * | 7/2001 | Slater et al. | 600/7 |
| 6,387,035 B1 | * | 5/2002 | Jung et al. | 600/3 |
| 6,436,068 B1 | * | 8/2002 | Bardy | 604/57 |
| 6,482,142 B1 | * | 11/2002 | Winkler et al. | 600/3 |
| 6,494,835 B1 | * | 12/2002 | Ciezki et al. | 600/439 |
| 6,800,055 B2 | * | 10/2004 | Amols et al. | 600/8 |
| 2003/0233136 A1 | | 12/2003 | Williams et al. | |
| 2005/0049508 A1 | * | 3/2005 | Forman et al. | 600/476 |
| 2007/0225544 A1 | * | 9/2007 | Vance et al. | 600/8 |

FOREIGN PATENT DOCUMENTS

| | | | |
|---|---|---|---|
| EP | 0 668 088 A | | 8/1995 |
| EP | 1 529 554 A | | 5/2005 |
| EP | 1529554 A1 | * | 5/2005 |
| WO | WO 02/40092 A | | 5/2002 |

OTHER PUBLICATIONS

Phillip James Muench, et al., Dose distributions produced by shielded applicators using 241 Am for intracavitary irradiation of tumors in the vagina, Med. Phys. 19 (5) Sep./Oct. 1992.

* cited by examiner

*Primary Examiner*—Charles A Marmor, II
*Assistant Examiner*—Catherine E Burk
(74) *Attorney, Agent, or Firm*—Boyle Fredrickson, S.C.

(57) ABSTRACT

Radioactive sources for implanting in tissue to treat tumors and to provide a directional dose to allow improved dose placement, particularly at the interface between healthy and diseased tissue.

5 Claims, 3 Drawing Sheets

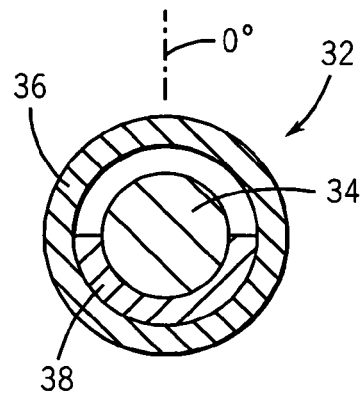
FIG. 3
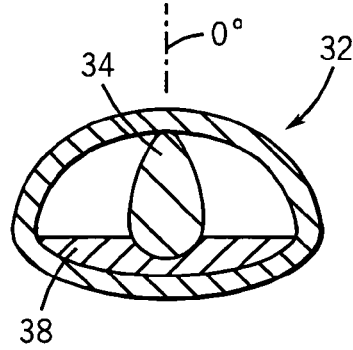
FIG. 4
FIG. 5
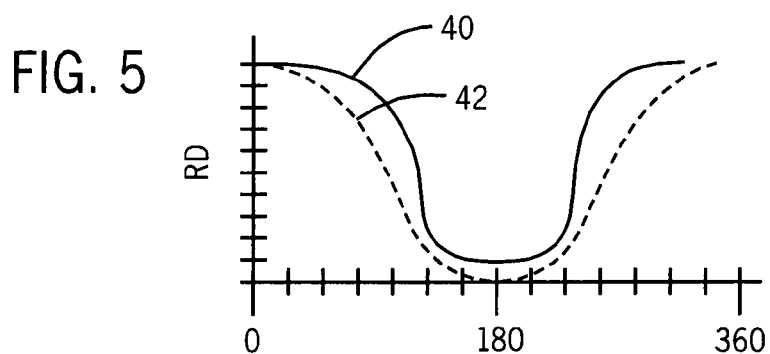
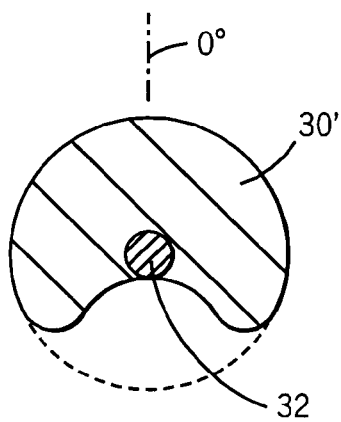
FIG. 6
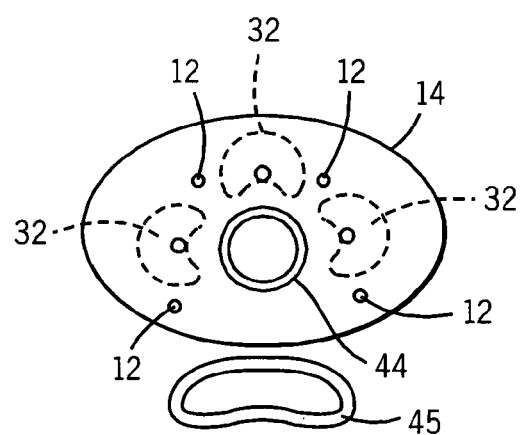
FIG. 7

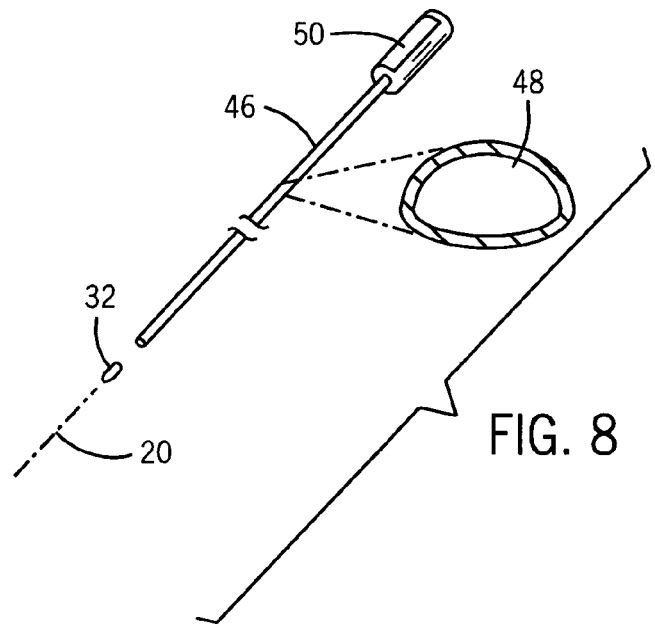
FIG. 8
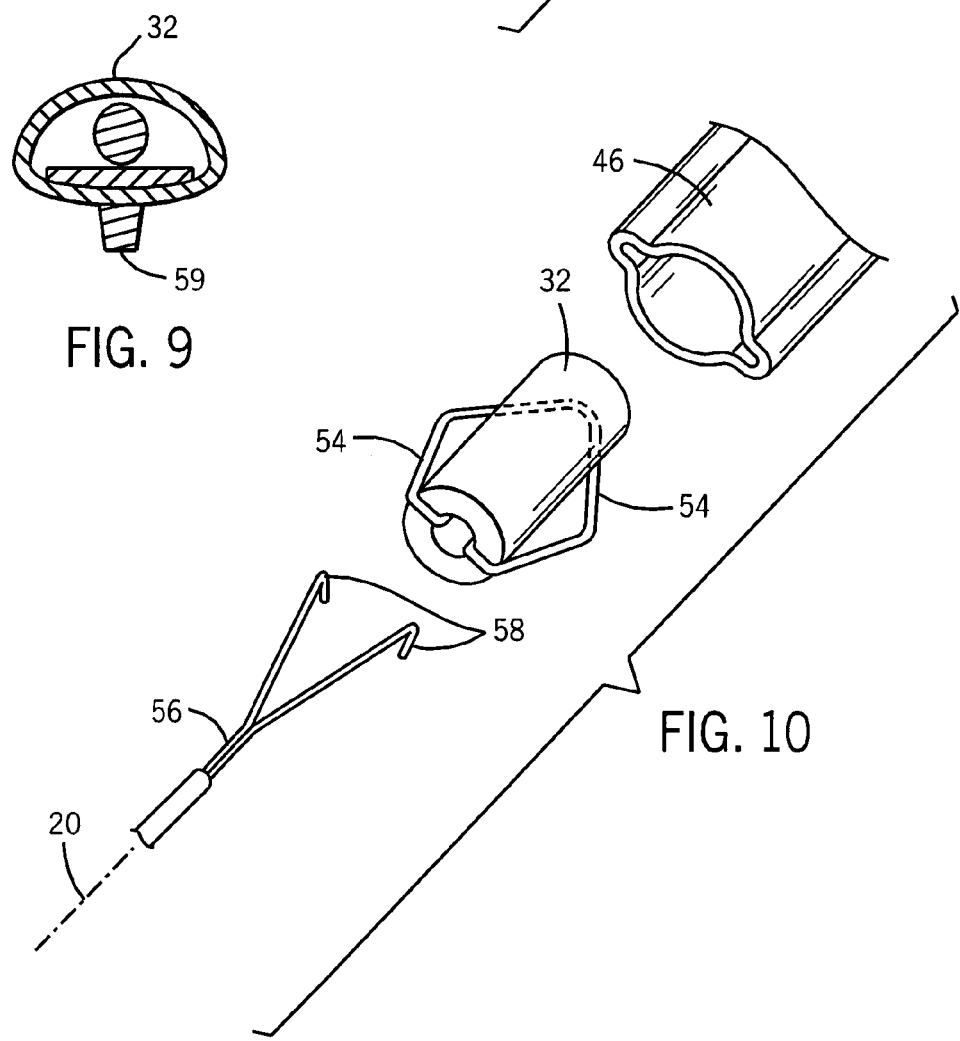
FIG. 9
FIG. 10

DIRECTIONALLY EMITTING RADIOACTIVE SOURCES FOR BRACHYTHERAPY

CROSS-REFERENCE TO RELATED APPLICATIONS

This application is based on provisional application 60/572,962 filed May 20, 2004 entitled "Directionally Emitting Radioactive Sources for Permanent Implantation".

STATEMENT REGARDING FEDERALLY SPONSORED RESEARCH OR DEVELOPMENT

This invention was made with United States government support awarded by the following agencies: DOE DE-FG07-01ID14104. The United States has certain rights in this invention.

BACKGROUND OF THE INVENTION

The present invention relates to radiation therapy principally for the treatment of cancer and benign diseases, and in particular, radioactive sources used in one radiation therapy technique termed brachytherapy.

Brachytherapy is radiotherapy where small, radioactive sources are placed into diseased tissues, in body cavities near disease, or in contact or close proximity to disease. Brachytherapy takes many forms, the most common of which are permanent implants, where the sources are left in place from the time of implantation for the life of the patient, or temporary implants, where the sources dwell in the treatment location for a specified time, after which they are removed. The temporary implants may be low dose-rate, where the sources stay in place for times on the order of a day to a week, or high dose-rate, where a treatment takes a matter of minutes. There is also a middle dose-rate region where treatments range from a couple of hours to just over a day.

One common example of a permanent implant occurs with treatment of cancer of the prostate. Prostate permanent implant brachytherapy is a radiation treatment technique in which radioactive sources are implanted directly into the prostate and left in place permanently. Typically, 50 to 100 small radioactive sources are implanted near the tumorous tissue.

The sources may be radioactive material absorbed onto small resin spheres contained within a titanium capsule or on the surface of a silver rod also sealed in titanium. The sources often use iodine-125 as the source material for the radiation, which has a half-life of approximately sixty days providing an average energy of emitted photons of approximately 27 keV, with commercial source strengths in the range of 0.2-1.0 mCi.

The sources, of a size 0.8 mm in diameter and 4.5 to 5 mm long, may be implanted using a hollow needle. The needle provides a lumen 1.3 to 1.5 millimeters in diameter and about 20 cm long into which the sources may be inserted along with spacers controlling their separation. The loaded needle is inserted into the patient, and then withdrawn, while a plunger ejects the contained sources.

The location of the radioactive sources is desirably selected to provide a prescribed dose to the diseased tissue of the prostate while sparing surrounding sensitive, critical tissue, for example, the urethra and rectum. Source placement in the region between sensitive tissue and diseased tissue is a compromise between providing sufficient dose to the diseased tissue and minimizing dose to the sensitive tissue.

Prostate cancer can also be treated using high dose-rate brachytherapy. In this case, needles are placed into the prostate and then connected to a treatment unit. The unit moves a very intense radioactive source through the needles, stopping at determined positions for times calculated to deliver the desired dose. The device steps the source through the first needle, retracts it and then moves the source through the next needle. This pattern continues until all needles have been accessed by the radioactive source and the treatment is concluded.

Many cancers are treated in a manner between the two described, where needles are placed into the target, and many sources are placed into the needles, with source strengths and positions calculated to deliver the desired dose in the prescribed time. The dose pattern emitted by these sources is isotropic relative to the lengthwise axis of the encapsulated cylindrically shaped source.

BRIEF SUMMARY OF THE INVENTION

The present inventors have developed a radioactive source having a directional radiation emission pattern that allows improved treatment of tissue at the interface between diseased and healthy, radiation-sensitive tissue. Orientation and retention of the sources in the desired orientation may be provided by external features on the sources serving to anchor the sources or orient them within the needle.

Specifically, the present invention provides a brachytherapy source for radiation treatment providing directional emission of radiation.

It is thus one object of at least one embodiment of the invention to provide improved control of a radiation dose providing sources with directional radiation emission patterns.

The directionality may provide a minimum emitted radiation at a first angle and a maximum emitted radiation at a second angle opposite the first angle.

Thus it is another object of at least one embodiment of the invention to provide sources uniquely suited for the region between healthy and tumorous tissue that can be used to create a sharper boundary in treatment between these two zones.

The sources may be adapted to slide through a needle for implantation with a longitudinal axis of the source extending along a lumen of the needle. The radiation may be directional in a plane perpendicular to the longitudinal axis so that rotation of the needle may orient the directionality of emission.

It is thus another object of at least one embodiment of the invention to provide a simple method of placing and orienting the sources.

The source may be comprised of a radioactive source with a shield partially blocking radiation from the radioactive source.

It is thus another object of at least one embodiment of the invention to provide a simple method of shaping the emission of the source using a shield.

The radioactive source and shield may be encapsulated in a biocompatible radiation permeable casing that does not follow the shape of the source and shield.

Thus it is another object of at least one embodiment of the invention to provide independence between the shape of the shield and radiation source and the shape of the source, the latter, which may be shaped for improved insertion, orientation, and retention.

The shield and source may be shaped and arranged with respect to each other to substantially maximize within material constraints a rate of change of emissions as a function of angle about the source.

It is thus another object of at least one embodiment of the invention to provide a large gradient in radiation with respect to angle for at least a portion of the radiation pattern for the source.

The source, when adapted to slide through a needle for implantation with a longitudinal axis of the source extending along a lumen of the needle, may be directional in a transverse plane perpendicular to the longitudinal axis.

It is thus another object of at least one embodiment of the invention to provide a method of controlling the angle of implanting of the sources with a needle.

The source may include at least one outwardly extending vane, guide, or anchor.

It is thus another object of at least one embodiment of the invention to provide a method of anchoring the sources against rotation in the patient for permanent implants. In another embodiment the outwardly extending vane can serve as a guiding mechanism for temporary implants as the source passes through a needle or catheter.

The vane may be fixed or expandable outward. In one embodiment, the vane is fixed to the source jacket or part of the jacket and remains extended at all times. In one embodiment, the vane may be soluble so as to dissolve after a period of time. In another embodiment, the vane may be a wire expanding from the source after insertion.

It is yet another object of at least one embodiment of the invention to provide several methods of rotationally stabilizing the source without hampering initial insertion of the source in tissue.

These particular objects and advantages may apply to only some embodiments falling within the claims and thus do not define the scope of the invention.

BRIEF DESCRIPTION OF THE DRAWINGS

FIG. 3 is a transverse cross-sectional view through a source of the present invention showing a shield layer between a core of radioactive material and an outer sheathing;

FIG. 4 is a cross-sectional view similar to that of FIG. 3 showing optimization of the core and shield to provide sharper demarcation in the emission zones;

FIG. 5 is plot of relative dose as a function of angle about the source within a transverse plane for the sources of FIGS. 3 and 4;

FIG. 6 is a figure similar to that of FIG. 2b showing the emission pattern for the source of FIG. 4;

FIG. 7 is a cross-section through the patient along an anatomical horizontal plane, showing placement of the multiple sources of the present invention in a ring about the urethra facing into the prostate;

FIG. 8 is a perspective view and cross-sectional expansion of a needle used for placing the source of FIG. 4;

FIG. 9 is a cross-section similar to that of FIGS. 3 and 4 showing use of a keel to prevent source rotation; and FIG. 10 is an exploded perspective view of an alternative embodiment of the source laterally expanding wire wings that press into the tissue to prevent rotation of the source and showing an insertion needle for inserting that source and a retractor hook used for removing or reorienting that source.

The above figures depict the embodiment of permanent implant brachytherapy and the delivery of the sources in this embodiment. Another embodiment is temporary implant brachytherapy. For this embodiment, the source design is essentially the same, however, the procedure for delivery is different and has been discussed in the background section. Another embodiment is for high dose-rate brachytherapy, in which embodiment the source is connected to a cable as discussed in the background section.

DETAILED DESCRIPTION OF THE PREFERRED EMBODIMENT

The detailed description describes permanent implant brachytherapy, however it will be understood to those of ordinary skill in the art that the sources and needles described may also be adapted for temporary implant brachytherapy as discussed in the previous section.

Figure 1:
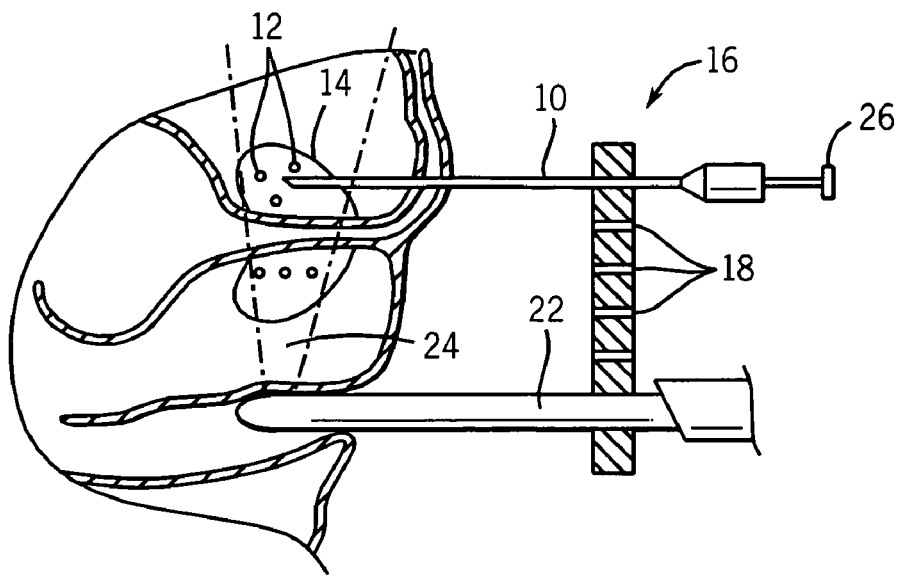
FIG. 1 is a fragmentary cross-sectional view taken along a mid-sagittal plane of a patient receiving radioactive sources for the treatment of the prostate.

Referring now to FIG. 1, a prostate brachytherapy uses a hollow needle 10 to place radioactive sources 12 within the prostate 14 transperineally.

The needle 10 may be guided by a plate 16 having a plurality of holes 18 placed at regular grid locations over the two dimensions of the plate 16. The plate 16 may be clamped to a transrectal ultrasonic probe 22 providing an ultrasonic beam 24 illuminating the prostate 14. The beam 24 provides a means of verifying the depth of placement of the sources 12 as they are ejected from the needle 10 by means of a plunger 26 fitting within the hollow shaft of the needle 10. In one technique, the sources 12 are placed within the needle 10 in a preconfigured separation enforced by non-radioactive spacers.

Figure 2A:
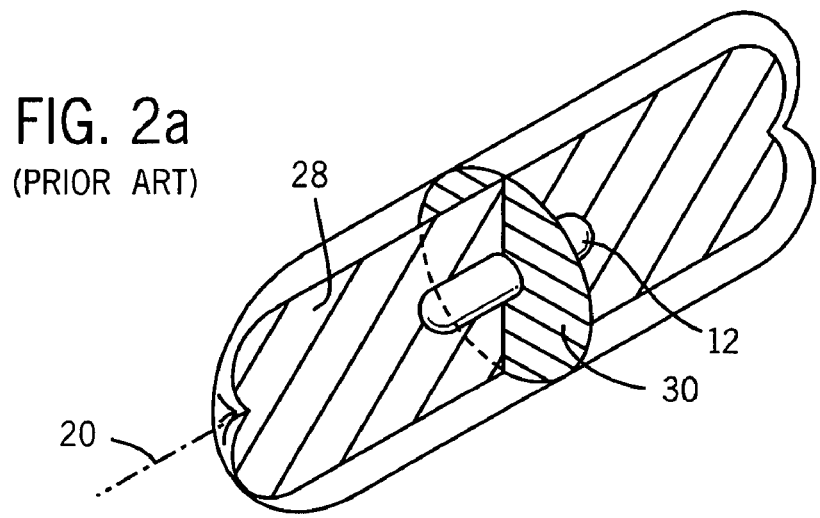
FIGS. 2a and 2b are superimposed perspective and transverse cross-sectional views, respectively, of a radiation source of the prior art, showing the pattern of radiation emission.

Referring now to FIG. 2, each of the sources 12 used in the prior art is roughly cylindrical in shape, the axis of the cylinder (termed henceforth "the longitudinal axis 20") aligning with the axis of a lumen of the needle 10 when the source 12 is placed within the needle 10.

A longitudinal radiation dose 28, defined by an isodose line lying in a plane along the longitudinal axis 20, is substantially symmetric about the source 12. In addition a transverse radiation dose 30 defined in a plane perpendicular to the longitudinal axis 20 is likewise symmetric, and in this case, circular. By symmetrical, it is meant that there exists a point were some measure of the dose (e.g. the distance from the point to an isodose line) is equally balanced on opposite sides of the point at all angles of interest. For the longitudinal radiation dose 28, the angles of interest are those laying in the relevant longitudinal plane for the transverse radiation dose 30, and the angles of interest are those lying in the relevant transverse plane.

Referring now to FIG. 3, a directionally emitting source 32 per the present invention provides a core radioactive source 34 positioned within a shell 36 of titanium or other biocompatible material. The source 34 may, for example, be a non-radioactive substrate material such as silver, polymer, or graphite coated with a radioactive material such as I-125 or Pd-103.

In a first embodiment, the shell 36 and source 34 are generally cylindrical. Positioned between the source 34 and the shell 36 is a shield 38, in this case, covering approximately 180 degrees of the cylindrical circumference of the source 34. Radiation emitted from the upper surface of the source 32 (designated as an azimuthal angle of zero degrees) is substantially unattenuated by the shield 38 whereas the shield 38 significantly reduces radiation emitted through the lower surface of the source 32. Generally, a variation in dose in excess of 5 to 1 may be obtained with reasonable shield thicknesses. A variation in radiation emission of at least 50% is preferred.

Referring now to FIG. 4, in an alternative embodiment, the circular cross-sectional areas of the source 34, the shell 36, and the accurate shape of the shield 38 are altered to sharpen the transition between the attenuated radiation from the bottom of the source 32 to the top of the source 32. This sharpening may be optimized through computer modeling, but in this embodiment, generally concentrates the radioactive surface area of the source 34 near the shield 38 and flattens the shield 38 so that the shield 38 diverges tangentially from the source 34 rather than wrapping around the source 34 in a cylindrical trough as per FIG. 3.

Referring to FIG. 5, a plot of relative dose (RD) as a function of azimuthal angle shows an optimized curve 40 produced by the source 32 of FIG. 4 having a steeper slope (i.e., rate of change of relative dose as a function of azimuthal angle) than unoptimized curve 42 produced by the source 32 of FIG. 3. This optimized curve 40 allows sources 32 to create a radiation dose pattern that more finely distinguishes between tissue that receives radiation and tissue that has minimal radiation exposure.

Figure 2B:
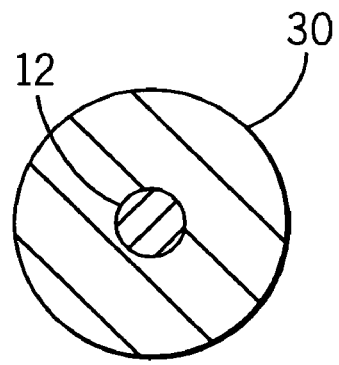

Referring to FIG. 6, a transverse radiation dose 30' for the sources 32 of FIGS. 3 and 4 is directional in the transverse plane in contrast to the symmetrical and circular transverse radiation dose 30 shown in FIG. 2b for the prior art.

Referring now to FIG. 7, sources 32 of the present invention, properly oriented, can provide a desired therapeutic dose of radiation to the prostate 14 while minimizing radiation dose to the urethra 44. In one example, the sources 32 are placed along a circular arc in tissue near an interface between the prostate 14 and the urethra 44, the arc having an open portion above the rectum 45. The front surfaces of the sources 32 defined by zero azimuthal angle are positioned to face outward away from the urethra 44.

The sources 32 may, for example, be integrated into conventional treatment planning by first placing the sources 32 as described, and then adding prior art sources 12 based on the fixed position of the initial sources 32. Multiple sources 32 may be placed in a needle 46 (FIG. 8) for implantation. The needle 46 may also hold standard sources 12 which may be specially prepared to have the same shape as the lumen of the needle 46 or which may have a different shape that nevertheless fits within the lumen of the needle 46 without fully conforming to the interior of the lumen. After each source 32 is ejected from the needle 46 by a plunger, the needle may be repositioned by drawing it along the needle axis and/or rotating the needle.

Referring now to FIG. 8, the sources 32 may be oriented by using a special needle 46 having a lumen with an asymmetric or noncircular cross-section 48 keyed to features of the source 32 (for example, conforming to the asymmetric cross-section of the source 32) to prevent rotation of the source within the needle 46. Indicia 50 may be placed on the needle 46 to indicate the zero azimuthal angle of the sources 32 as they are inserted within the needle 46. Insertion of the needle 46 into the patient may thus be with a controlled orientation or the needle 46 may be rotated after insertion or between discharge of various sources to control the orientation of those sources 32.

Generally the needle 46 may be simply extruded according to the outline of the cross-section of the sources 32 in the transverse plane and thus may have an outer surface generally conforming to the cross-section of the lumen with constant wall thickness. Alternatively, the outer surface may adopt an alternative cross-section, for example, a cylindrical cross-section or the like.

Referring now to FIG. 9, the source 32 may stably resist rotation within tissue of the patient based on its asymmetric outline or other anchoring mechanisms. In one embodiment, the anchoring mechanism may be the addition of a transversely extending keel 52 or fin that may engage tissue to prevent axial rotation of the source 32. The keel 52 may be formed integrally with the shell 36 or may be added in a later manufacturing step. In one embodiment, the keel or fin 52 may be a biodissolving material that provides stabilization until scar tissue can lock the source 32 into position. In one embodiment, the keel or fin 52 may serve as a guide for temporary implant sources.

Referring now to FIG. 10, the stabilization mechanism for the source 32 need not be fixed, but may comprise extensible wings 54 formed in one embodiment from "shape memory" wire (an NiTi alloy) or spring wire either that may crush inward slightly when the source 32 is inserted into the needle 46 and then spring outward to engage tissue with an outward biasing force. The lumen of the needle 46 may be adjusted appropriately to accommodate these anchoring mechanisms.

In the embodiment of FIG. 10, the outwardly extending wings 54 provide a location by which to grip the source 32 with a retractor tool 56 having a pair of hooks 58 that may engage the wings 54 when extended for withdrawal of the source 32. In the example of FIG. 10, the force of the hooks 58 on the wings 54 is such as to retract the wings 54 somewhat to improve their movement through the tissue.

The present invention is not limited to use with the prostate, but may be used in any brachytherapy source application. Other applications include breast, lung, esophagus, larynx, and gynecological applications.

It is specifically intended that the present invention not be limited to the embodiments and illustrations contained herein, but include modified forms of those embodiments including portions of the embodiments and combinations of elements of different embodiments as come within the scope of the following claims.

We claim:

1. A brachytherapy system comprising
a plurality of radiation sources having an axis and non-circular cross section perpendicular to that axis, the radiation source providing a predetermined directional emission of radiation varying with angles about the axis
a needle adapted for penetration of tissue and rotation along a needle axis therein and implantation of the radiation sources into the tissue when inserted wherein the needle provides a noncircular lumen having a cross section keyed to the non-circular cross sections of the radiation sources to slideably receive the radiation sources and to prevent rotation of the radiation sources about the axis with respect to the needle when the radiation sources are slid within the needle lumen the prevention of rotation resulting from a geometric interference between lumen walls and the non circular cross section of the radiation sources, and wherein the needle has an open distal end for ejection of the radiation sources into tissue;
whereby angulation of the radiation source may be adjusted by rotation of the needle during implantation of successive seeds radiation sources;
wherein the radiation sources are physically independent radioactive elements adapted for retention in the tissue after removal of the needle.

2. The brachytherapy system of claim 1 wherein the needle includes a distal portion remaining outside a human body when the radioactive sources are being implanted and wherein the distal portion includes a marking having a predetermined relationship to the lumen indicating an angulation of the radioactive sources within the lumen.

3. The brachytherapy system of claim 1 wherein the radiation sources are radioactive seeds with an asymmetric shield partially blocking radiation from the radioactive source; and wherein a radioactive portion of the seeds has a non-circular cross-section taken across the longitudinal axis providing a sharper transition in the variation of radiation than a circular cross section.

4. The brachytherapy system of claim 3 wherein the asymmetrical shield is substantially flat.

5. The brachytherapy source of claim 1, wherein the cross section of the outer surface of the needle is different than the cross section of the lumen thereof.

* * * * *